(12) United States Patent
Foster

(10) Patent No.: US 8,847,163 B2
(45) Date of Patent: Sep. 30, 2014

(54) METHOD AND APPARATUS FOR ABSORPTION SPECTRA ANALYSIS

(75) Inventor: Kevin Anthony Foster, Aylesford (GB)

(73) Assignee: Evoqua Water Technologies LLC, Alpharetta, GA (US)

( * ) Notice: Subject to any disclaimer, the term of this patent is extended or adjusted under 35 U.S.C. 154(b) by 1126 days.

(21) Appl. No.: 12/744,404

(22) PCT Filed: Nov. 21, 2008

(86) PCT No.: PCT/EP2008/065971
§ 371 (c)(1),
(2), (4) Date: Oct. 20, 2010

(87) PCT Pub. No.: WO2009/068477
PCT Pub. Date: Jun. 4, 2009

(65) Prior Publication Data
US 2011/0040494 A1  Feb. 17, 2011

Related U.S. Application Data

(60) Provisional application No. 60/990,127, filed on Nov. 26, 2007.

(51) Int. Cl.
*G01N 21/33* (2006.01)
*G01N 21/17* (2006.01)
*G01J 3/42* (2006.01)
*C02F 1/00* (2006.01)
*G01N 21/31* (2006.01)
*C02F 1/76* (2006.01)
*G01N 33/18* (2006.01)

(52) U.S. Cl.
CPC ............. *G01N 21/33* (2013.01); *G01N 21/17* (2013.01); *G01J 3/42* (2013.01); *C02F 1/008* (2013.01); *G01N 21/314* (2013.01); *C02F 1/76* (2013.01); *G01N 33/1826* (2013.01); *C02F 2209/29* (2013.01)
USPC .................................................... 250/339.12

(58) Field of Classification Search
CPC .............................. G01N 21/17; G01N 21/33
USPC ......................................... 250/339.12; 702/25
See application file for complete search history.

(56) References Cited

U.S. PATENT DOCUMENTS 5,630,987 A    5/1997  Briggs
6,642,521 B2 * 11/2003  Namose et al. .......... 250/339.09

(Continued)

OTHER PUBLICATIONS

Benjathapanlun N et al: "Binary encoded 2nd-differential spectrometry using UV-Vis spectral data and neural networks in the estimation of species type and concentration", IEE Proceedings: Science, Measurement and Technology, IEE, Stevenage, Herts, GB, vol. 144, No. 2, Mar. 14, 1997, pp. 73-80, XP006008985 ISSN:1350-2344, p. 73, col. 2, line 5—p. 78, last line, figures 1, 4-10,12 tables 1-5; Others; 1997.

(Continued)

*Primary Examiner* — David Porta
*Assistant Examiner* — Faye Boosalis

(57) ABSTRACT

A method and apparatus is disclosed for resolving absorption spectra such as ultraviolet or visible spectra having individual peaks attributable to more than one component in a sample mixture. The invention exploits the observation that the peak wavelength varies according to the component concentrations, providing the basis for an initial estimate of these. A curve fitting exercise is performed for a range of possible concentrations encompassing the initial estimates so that the a theoretical spectrum having the closest match to that observed provides for a refined estimate of component concentrations.

21 Claims, 6 Drawing Sheets

(56) References Cited

U.S. PATENT DOCUMENTS

2002/0130069 A1 9/2002 Moskoff
2007/0045542 A1* 3/2007 Hashmonay ............ 250/339.12

OTHER PUBLICATIONS

Qiang Z and Adams C D: "Determination of Monochloramine Formation Rate Constants with Stopped-Flow Spectrophotometry" Environ.Sci. Technol., [Online] vol. 38, 2004, pp. 1435-1444, XP002519709 Retrieved from the Internet: URL:http://pubs.acs.org/doi/abs/10.1021/es0347484?journalCode=esthag&quickLinkVolume=38&quickLinkPage=1435&volume=38>,[retrieved on Mar. 17, 2009] p. 1437, col. 2, line 1—p. 1439, col. 1, line 16; figures 1,2; Others; 2004.

Watts et al: "Chlorine photolysis and subsequent OH radical production during UV treatment of chlorinated water" Water Research, Elsevier, Amsterdam, NL, [Online] vol. 41 , No. 13, Jun. 8, 2007, pp. 2871-2878, XP022109981, ISSN:0043-1354, Retrieved from the internet: URL:http://www.sciencedirect.com/science?_ob=PublicationURL&_tockey=%23TOC%235831%232007%-23999589986%23660557%23FLA%23&_cdi=5831&_pubType=J&_acct=C000049880&_version=1&_userid=9877668&md5=6e3d15f3dd8112f9447e55aaa6aa8fcl> [retrieved on Mar. 17, 2009] p. 2872, col. 1, last line—p. 2874, col. 2, line 50; figures 1-4; table 1; Others; 2007.

* cited by examiner

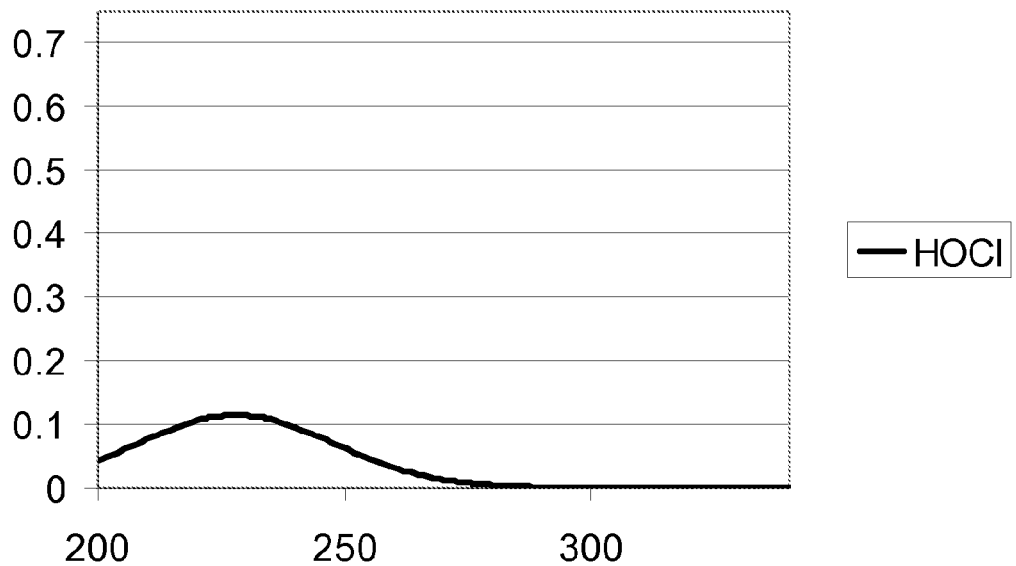
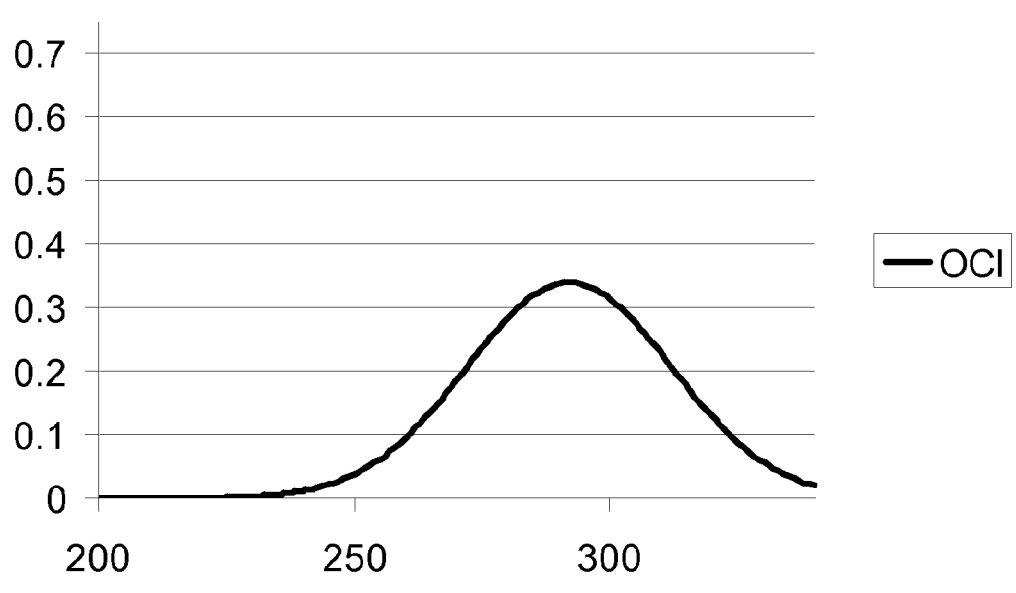

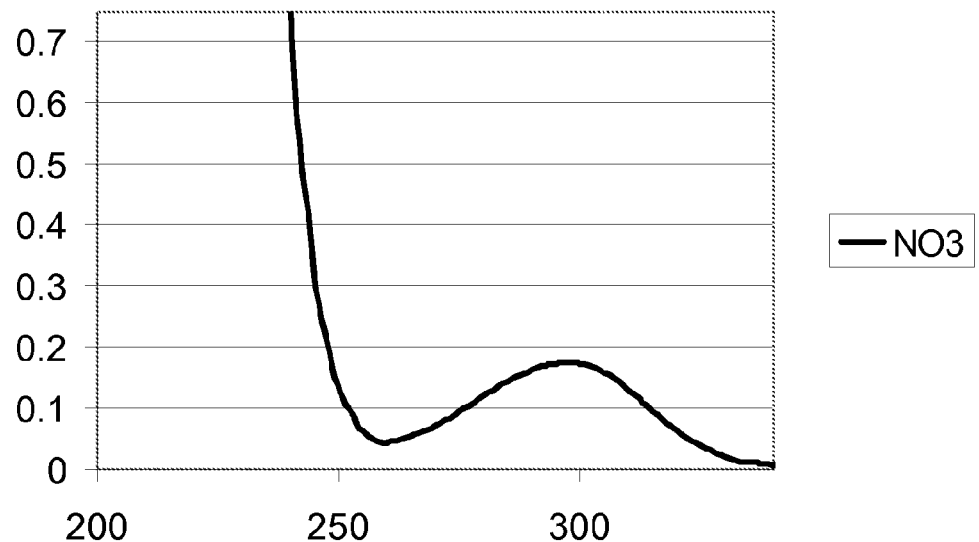
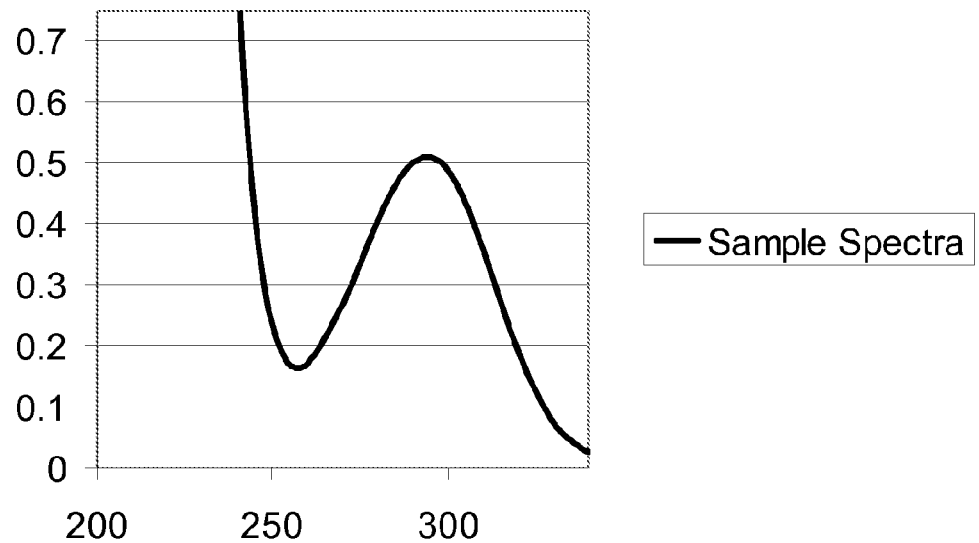

METHOD AND APPARATUS FOR ABSORPTION SPECTRA ANALYSIS

CROSS REFERENCE TO RELATED APPLICATIONS

This application is a U.S. national stage application and claims the benefit under 35 U.S.C. §371 of International Application No. PCT/EP2008/065971 filed on Nov. 21, 2008, entitled METHOD AND APPARATUS FOR ABSORPTION SPECTRA ANALYSIS, which claims the benefit under 35 U.S.C. §119(e) of U.S. Provisional Application Ser. No. 60/990,127 entitled SPECTROSCOPIC CHLORINE ANALYZER, filed on Nov. 26, 2007, each of which is herein incorporated by reference in their entirety and to which this application claims the benefit of priority.

The invention is concerned with the field of absorption spectroscopy.

The use of spectroscopic techniques to identify substances or components of a mixture is well known and documented. Very generally, in absorption spectroscopy, a sample is irradiated with electromagnetic radiation having a range of wavelengths/frequencies and radiation of certain wavelengths within the range interacts with the sample.

For example, in Ultraviolet (UV) spectroscopy, radiation of certain wavelengths has the correct energy to cause shifts in the energy levels of outer shell electrons in atoms of the sample. In Infrared (IR) spectroscopy, radiation has the correct energy to stimulate inter-atomic vibration.

These interactions between the sample and radiation give rise to absorption of radiation by the sample at the wavelengths having the correct energy. A detector arranged to measure the intensity of radiation that has passed through the sample provides an indication of the wavelengths at which absorption occurs along with the degree of absorption.

The data gathered by the detector is typically presented as a plot of absorption versus wavelength (or energy) of the radiation, this presentation being known as an absorption spectrum for the sample.

As an alternative to the absorption spectrum, the data gathered by the detection could be presented as a plot of transmission (of radiation) versus wavelength/energy, the presentation being known as a transmission spectrum. However, in terms of the information being presented, the absorption spectrum and transmission spectrum may be regarded as equivalent and, as done herein, reference to one of these terms should be construed as reference to both.

In many cases, the absorption spectrum associated with a particular compound or chemical species provides a reliable means of identification/quantification but in others, the results are complicated when various components of a mixture exhibit absorption at the same or nearly the same wavelengths.

Moreover, the absolute value at which absorption occurs due to (say) a particular electronic shift may vary with other conditions such as pH or the presence of other species.

The practice of adding chlorine to water to act as disinfectant has been well established for many years. There is an associated need to analyse water for chlorine content which has traditionally been met using techniques that involve chemical reagents and buffering. These techniques are time consuming and expensive and do not readily lend themselves to rapid, in-field testing by mobile personnel.

There exists a long standing desire for a method of chlorine analysis that does not involve chemical reagents and can be conveniently carried out in the field, for example, by agents of the water supply industries.

Methods involving spectroscopic analysis have the potential to meet this long standing need, but absorbance values for levels found in drinking water (typically <1 mg/l) are too small be measured using a typical 10 mm cell.

Moreover, problems of the type previously alluded to are met as $NO_3$ effectively masks the absorbance exhibited by the chlorine species.

Chlorine dissolved in water exists in two forms, namely hypochlorous acid (HOCl) and hypochlorite ($OCl^-$). Each of these species exhibits absorbance in the UV range of electromagnetic radiation. In conditions of low pH, (<pH 6), the HOCl form predominates at a peak wavelength of 228 nm and in conditions of high pH, (>pH 9), the $OCl^-$ form predominates at a peak wavelength of about 292 nm. For pH values between 6 and 9, the spectrum is the sum of absorbances around these two wavelengths.

Moreover, the $NO_3^-$ species typically coexists with the chlorine species in water. $NO_3^-$ exhibits peak absorbances at 210 nm and 300 nm and these peaks overlap with those associated with chlorine in a UV spectrum.

According to the invention these, and other problems associated with the prior art are addressed by a method of estimating the respective concentration of components in a solution comprising the steps set out in claim 1 attached hereto.

According to a second aspect of the invention, apparatus for estimating the respective concentrations [X] and [Y] of at least two components, X and Y, in a solution comprises the features set out in claim 10 attached hereto.

The apparatus will now be described with reference to the following figures in which:

FIG. 1 shows typical UV spectra for each of the components present when chlorine is dissolved in water, along with a single spectrum derived from all components;

Figure 2A:
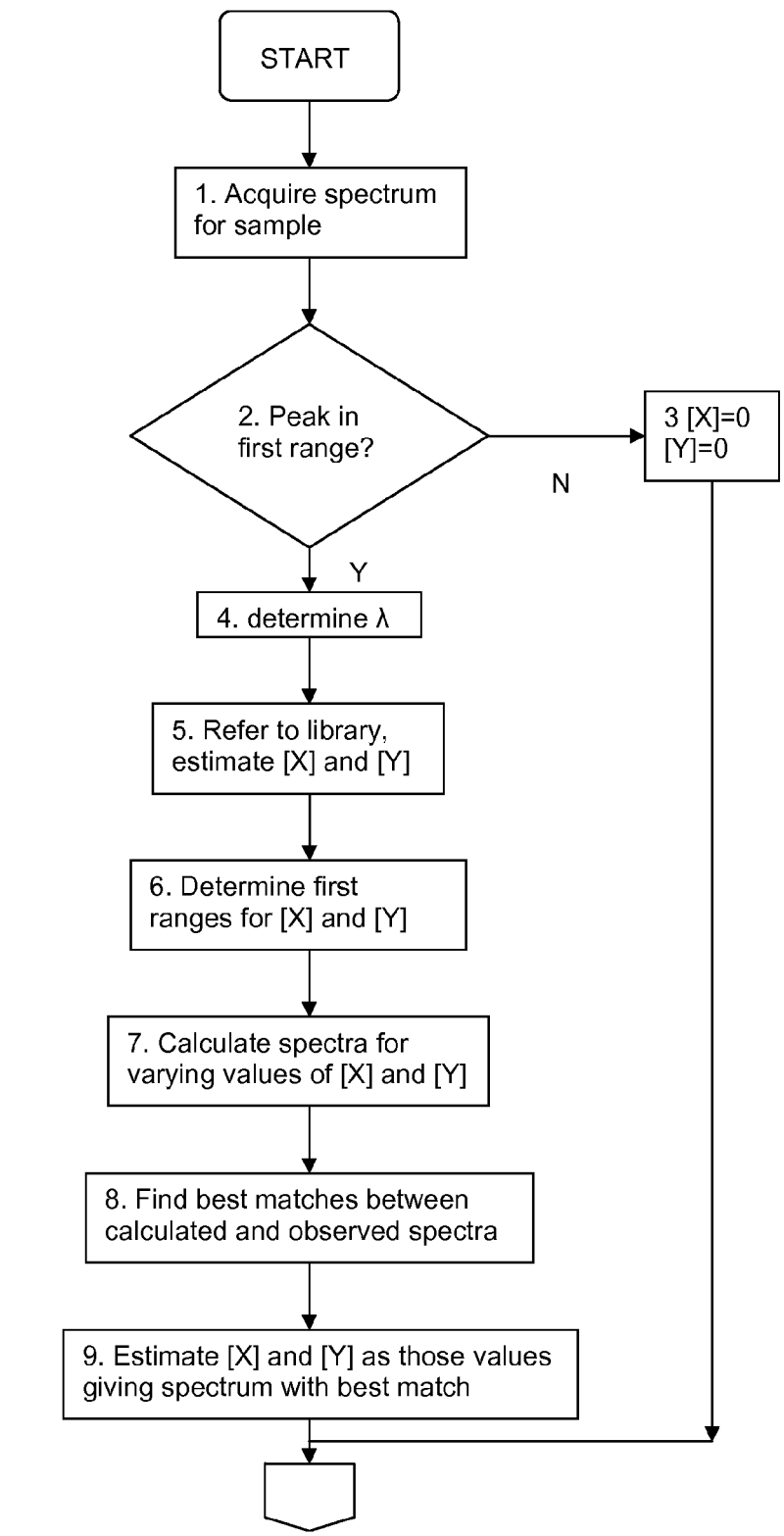
FIG. 2 is a flowchart illustrating the method of the invention.

Referring to FIG. 1*a* the peak absorbance for the HOCl species occurs at about 235 nm and FIG. 1*b* shows a peak absorbance for the $OCl^-$ species at about 292 nm.

FIG. 1*c* shows a peak absorbance for $NO_3^-$ of about 300 nm along with increasing absorbance as the wavelength falls below about 250 nm. 1*d* shows that when these species coexist in a sample, a single peak is seen at about 290 nm (due to $OCl^-$ and $NO_3^-$) and the absorbance due to HOCl is masked by the absorbance due to $NO_3^-$ below about 250 nm.

The method of the present invention uses the graphical technique of curve fitting. In principle, it is possible to perform a series of calculations of absorbance across the wavelength range of the observed spectrum for a sample. These calculations would be done for varying concentrations of the various components HOCl, $OCl^-$ and $NO_3^-$ and extrapolated to produce a series of theoretical spectra, each spectrum being associated with a particular combination of component concentrations.

A curve fitting technique such as a least squares fit would then be used to determine which of the calculated spectra most closely fits the observed spectrum and the component concentrations giving rise to that calculated spectrum are used as an estimate of the component concentrations in the sample.

In practice, however, the inventors have found that the processing demands made by such an approach are prohibitive. For the purpose of chlorine monitoring in a domestic water supply, a typical calculation would need to consider a range of 0 to 50 mg/l in steps of 0.1 mg/l for $NO_3^-$, 0 to 2 mg/l in steps of 0.01 mg/l for $OCl^-$ and a range of 0 to 2 mg/l in steps of 0.01 mg/l for HOCl. This would typically be done for each whole number value of wavelength between 200 nm and 400 nm giving rise to $2 \times 10^7$ calculations. Additionally, 200 calculations must be stored and compared to the last 200 to find a least squared fit, introducing another factor of 200.

The inventors have developed a method including a step which drastically reduces the number of calculations necessary to perform a curve fitting analysis to the degree of accuracy desired. Where an absorption spectrum includes a peak that is attributable to more than one component of a sample, the inventors have observed that the precise wavelength of that peak varies with the respective concentrations of those components.

This observation forms the basis of an initial estimate of component concentrations, made by comparing the observed spectrum for the sample with a library of reference data.

This initial estimate can be used to define much narrower ranges for the component concentrations over which the calculations necessary for the curve fitting exercise need to be performed.

After the concentration of a component has been estimated from a first peak in this way, that estimate can be used to estimate the contribution to a second peak by that component. When that contribution is subtracted from the second peak, the difference can form the basis of an estimate for the concentration of a third component.

Figure 2B:
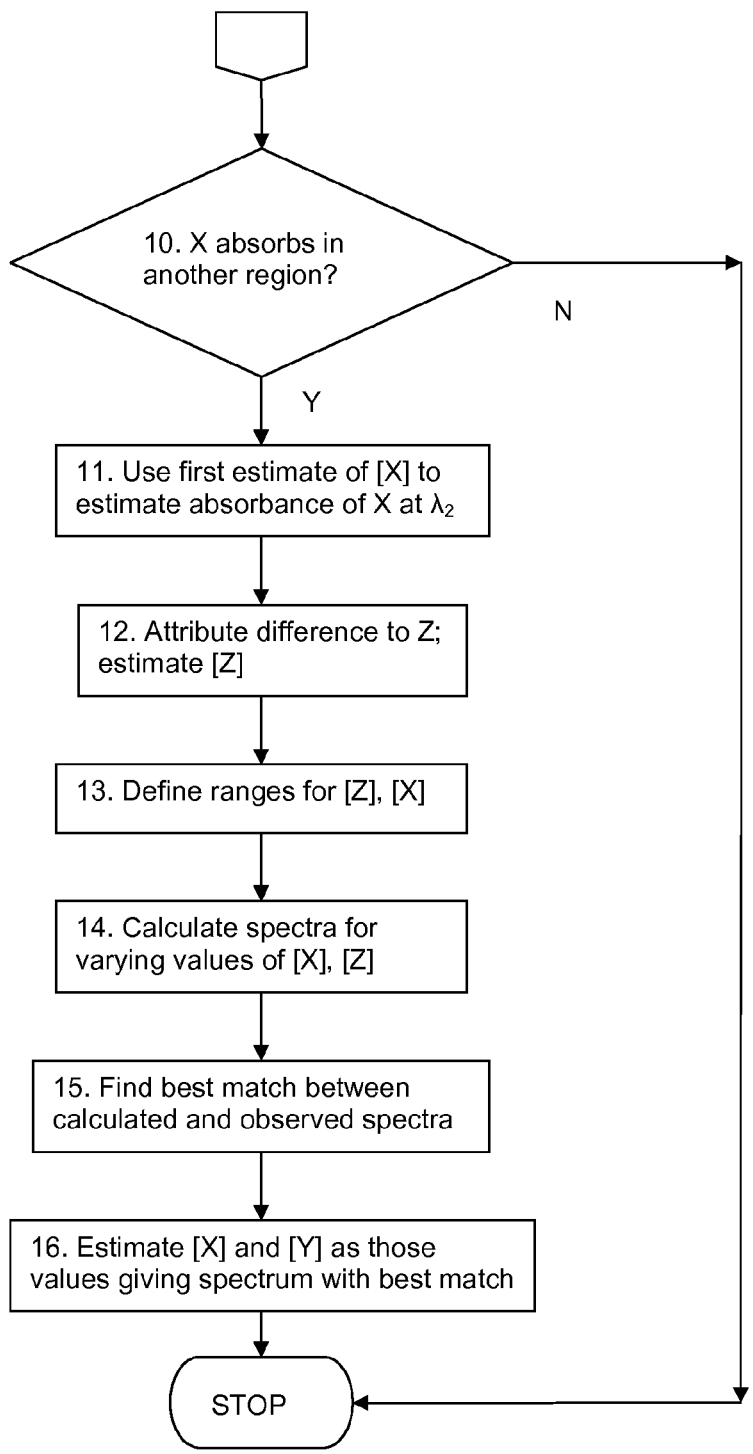

Referring to FIG. 2, analysis of a sample according to the method of the invention begins with acquisiton of an absorption spectrum for the sample at 1. At 2, a determination is made of whether a peak exists in the acquired spectrum, within a first predefined range in which absorption would be observed for two components of interest, X and Y. For the analysis of chlorine in water, X would be $NO_3^-$, Y would be $OCl^-$ and the first predetermined range would include values between 290 nm and 320 nm.

If no such peak is found, the values for the concentrations of X and Y, denoted by [X] and [Y] respectively, are assumed to be zero (step 3) and the third stage of the method can be initiated at step 10.

If an absorption peak is observed in the first predefined range, the wavelength of the peak is determined at 4.

Comparison of this wavelength with previously obtained reference data at 5 provides a first estimate for the values of [X] and [Y]. Typically, the reference data might exist as a look-up table which offers a number of possible values for each of [X] and [Y]. In its simplest form, the invention provides a basis for estimating [X] and [Y] using the look-up table, for example by taking an average of the possible values offered by the table.

In a second stage of the method, the initial estimate obtained at 5 is further refined by first defining ranges for possible values of [X] and [Y] (at 6) around the estimates obtained at 5 and then calculating the spectra (at 7) that would be expected from solutions having values across these ranges. The actual number of spectra calculated depends on the degree of accuracy required. Typically a set of values across each range would be defined (e.g. by starting at the lowest value in the range and repeatedly incrementing that value by a chosen amount) and spectra would be calculated for all combinations of a value from the range for [X] with a value from the range for [Y].

Spectra can be calculated for a chosen set of concentrations using response factors (absorbances) known in the literature for the components of interest.

At 8, the calculated spectra are compared with the acquired spectrum for the sample to find that having the closest match. The methods by which such a comparison may be made are well documented and known to a person skilled in the art. In a crude form, the comparison could be made by a visual inspection but a more sophisticated approach would employ mathematical techniques such as a least squares analysis.

At 9, a revised estimate for [X] and [Y] is derived from the values of [X] and [Y] giving the calculated spectrum having the best match with the acquired spectrum for the sample.

At 10, a third stage of the method can be initiated by determining whether absorption is observed in the acquired spectrum for the sample, in a second predefined range in which absorption would be observed for one of the components, X.

If such absorption is observed, then at 11, the contribution to that peak due to X is estimated using the previously obtained value of [X] and a previously known absorbance for X at a wavelength within the second range.

Having subtracted the contribution due to X, the remaining absorption is attributed to a third component Z, and an estimate of [Z] is estimated therefrom (12).

The concentration estimates may be further refined by initiating a fourth stage of the method at 13, where a range of possible values for [Z] and a new range of possible values fo [X] are defined to include the most recent estimates of [Z] and [X] respectively.

The exercise of calculating spectra is repeated for combinations of values from these ranges at 14 before a curve fitting exercise is performed at 15 to determine the combination of values of [X] and [Y] giving a spectrum which most closely resembles the acquired spectrum for the solution at 16.

Where the sample comprises chlorine dissolved in water, Z would be HOCl and absorption would be observed below 250 nm at step 10. The absorption due to X would be preferrabley be calculated (step 11) for a wavelength of between 230 nm and 250 nm, more preferrably between 235 nm and 245 nm most preferrably at 240 nm.

There now follows sample algorithm listing used for the determination of chlorine and nitrate in water.

The algorithm defines the response for a 30 cm path length cell. The absorption coefficients used are for a specific cell. According to practice well known in the art, a Nitrate ion standard of 30 parts per million is passed through the cell and the absorbance measured. Comparison of the observed absorbtion coefficient for Nitrate with the literature value yields a correction factor which is applied to the literature values of absorption coefficients for other species. The corrected absorption coefficients for the other species are then applied to the observed absorptions for these species to calculate concentrations.

The method is effective with cells having path lengths up to 100 cm.

To use for other path lengths, all calculated absorbance values should be factored by:

Actual path length/30.

For example, for a 100 cm cell, the definitions and absorbances below would be multiplied by 3.333.
Requirements for the Algorithm.

Define the Nitrate ($NO_3^-$), hypochlorite ($OCl^-$) and hypochlorous absorbance curves. Use these equations when calculation of [$NO_3^-$], [$OCl^-$] or [HOCl] is required 1. Define the Nitrate Absorbance Spectrum for 30 mg/l $$NO3 = (-3.19956858631723E\text{-}03) + (0.172085985390831/(1+\_Exp(-(x-296.404251810163+33.5223979282129/\_2)/9.85592846938872)))*(1-1/(1+\_Exp(-(x-296.404251810163-33.5223979282129/\_2)/6.84378175991155)))$$

Where x is the wavelength at which to calculate the absorbance

Converts the Nitrate 30 mg/l absorbance nitrate current mg/l to give theoretical absorbance for the current nitrate mg/l $$NO3 = NO3*(no3\_current/30)$$

2. Define the Hypochlorite Absorbance Spectrum for 5 mg/l $OCl1=(x-87.74559748588*(-6.23611708355894)/(2*\_9.47786188703371)-288.591861465584)/\_87.74559748588$ $OCl2=(-3.35605864187096E-04)+0.917441368457116*(1+\_OCl1*OCl1)^{\wedge}(-9.47786188703371)*\text{Exp}(-(-\_6.23611708355894)*(Atn(N)+Atn((-6.23611708355894)/\_(2*9.47786188703371))))/(1+(-\_6.23611708355894)*(-6.23611708355894)/(4*\_9.47786188703371*9.47786188703371))^{\wedge}(-\_9.47786188703371)$ Converts the Hypochlorite 5 mg/l absorbance Hypochlorite current mg/l to give theoretical absorbance for the current Hypochlorite mg/l $OCl2=OCL2*(ocl\ \text{current}/5)$ 3. Define Hypochlorous Absorbance Spectrum for 2 mg/l $HOCl1=0+0.167666162248925*\text{Exp}(-0.5*(\text{Abs}(x-227.464166361418)/17.5217273526745)^{\wedge}2.24405372401415)$ Converts the Hypochlorous 2 mg/l absorbance Hypochlorous current mg/l to give theoretical absorbance for the current Hypochlorous mg/l $HOCl=HOCl*(hocl\_\text{current}/(2))$ Algorithm Stage 1

1. Find peak in region 290-320 nm.
2. If no peak—Nitrate $[NO_3^-]=0.00$ mg/l and Hypochlorite $[OCl^-]=0.00$ mg/l. Go to STAGE 3
3. If peak present, the wavelength and maximum absorbance defines the possible values of $[NO_3^-]$ and $[OCl^-]$. Use the following the peak wavelength with the table 1 to determine an estimated range for $[NO_3^-]$ and $[OCl^-]$.

TABLE 1

| OCl | NO3 | | | | | | | | | | |
|---|---|---|---|---|---|---|---|---|---|---|---|
| | 0 | 5 | 10 | 15 | 20 | 25 | 30 | 35 | 40 | 45 | 50 |
| 0 | 289 | 298 | 298 | 298 | 298 | 298 | 298 | 298 | 298 | 298 | 298 |
| 0.1 | 289 | 295 | 296 | 297 | 297 | 297 | 297 | 298 | 298 | 298 | 298 |
| 0.2 | 288 | 293 | 295 | 296 | 296 | 297 | 297 | 297 | 297 | 297 | 297 |
| 0.3 | 288 | 292 | 294 | 295 | 296 | 296 | 296 | 297 | 297 | 297 | 297 |
| 0.4 | 288 | 291 | 293 | 294 | 295 | 295 | 296 | 296 | 296 | 296 | 297 |
| 0.5 | 288 | 291 | 292 | 293 | 294 | 295 | 295 | 296 | 296 | 296 | 296 |
| 0.6 | 288 | 291 | 292 | 293 | 294 | 294 | 295 | 295 | 296 | 296 | 296 |
| 0.7 | 288 | 290 | 292 | 293 | 293 | 294 | 294 | 295 | 295 | 295 | 296 |
| 0.8 | 288 | 290 | 291 | 292 | 293 | 294 | 294 | 295 | 295 | 295 | 295 |
| 0.9 | 288 | 290 | 291 | 292 | 293 | 293 | 294 | 294 | 295 | 295 | 295 |
| 1 | 288 | 290 | 291 | 292 | 292 | 293 | 293 | 294 | 294 | 295 | 295 |
| 1.1 | 288 | 290 | 291 | 291 | 292 | 293 | 293 | 294 | 294 | 294 | 295 |
| 1.2 | 288 | 290 | 291 | 291 | 292 | 292 | 293 | 293 | 294 | 294 | 294 |
| 1.3 | 288 | 290 | 290 | 291 | 292 | 292 | 293 | 293 | 294 | 294 | 294 |
| 1.4 | 288 | 290 | 290 | 291 | 292 | 292 | 293 | 293 | 293 | 294 | 294 |
| 1.5 | 287 | 290 | 290 | 291 | 291 | 292 | 292 | 293 | 293 | 293 | 294 |
| 1.6 | 287 | 289 | 290 | 291 | 291 | 292 | 292 | 293 | 293 | 293 | 294 |
| 1.7 | 287 | 289 | 290 | 291 | 291 | 292 | 292 | 292 | 293 | 293 | 293 |
| 1.8 | 287 | 289 | 290 | 291 | 291 | 292 | 292 | 292 | 293 | 293 | 293 |
| 1.9 | 287 | 289 | 290 | 290 | 291 | 291 | 292 | 292 | 293 | 293 | 293 |
| 2 | 286 | 289 | 290 | 290 | 291 | 291 | 292 | 292 | 292 | 293 | 293 |

The table will produce a range of figures. For example 297 is highlighted and shows the possible values of $NO_3^-$ and $OCl^-$.

END OF STAGE 1

Stage 2

The range of vales obtained at the end of stage 1 can then be used in the following equation $\text{Calc abs}=((ty*0.0044))+((tx/1)*0.0177)$ where tx defines the $OCl^-$ value in mg/l and ty defines the $NO_3^-$ value in mg/l The upper and lower limits for $NO_3^-$ and $OCl^-$ are defined as the closest Calc abs value just below the measured max abs and just above the measured max abs.

Redefine upper and lower $OCl^-$ limits at +/−0.1 mg/l

Loop for the range of hypochlorite in steps of 0.1 mg/l

Loop for the range of nitrate in steps of 1 mg/l

Loop for range 230 to 340 nm

Calculate the $NO_3^-$ absorbance value for each wavelength for intervals of 1 nm Calculate the $OCl^-$ absorbance value for each wavelength for intervals of 1 nm Sum the two.

Calculate the difference at each wavelength between the measured and the calculated absorbance.

Sum the square of the differences over the complete wavelength range.

If this is the smallest difference so far, store this number and the corresponding nitrate and hypochlorite value.

Set upper and lower nitrate as +/−1 mg/l from previous iteration.

Set upper and lower hypochlorite as +/−0.1 from previous iteration.

Loop for the range of hypochlorite in steps of 0.01 mg/l

Loop for the range of nitrate in steps of 0.1 mg/l

Loop for range 230 to 340 nm

Calculate the $NO_3^-$ absorbance value for each wavelength for intervals of 1 nm Calculate the $OCl^-$ absorbance value for each wavelength for intervals of 0.1 nm Sum the two.

Calculate the difference at each wavelength between the measured and the calculated absorbance.

Sum the square of the differences over the complete wavelength range.

If this is the smallest difference so far, store this number and the corresponding nitrate and hypochlorite value in mg/l.

END OF STAGE 2

Stage 3

Calculate the nitrate absorbance at 240 nm.

Subtract this value from the absorbance at 240 nm.

The remaining absorbance at 240 nm is the absorbance due to HOCl.

Convert to approximate HOCl concentration by $$HOCl = HOClabs/(114*30)$$

This gives HOCl in mg/l.

END OF STAGE 3

Stage 4

Define HOCl range as +/−0.25 of this value

Define $NO_3^-$ range as +/−5 of calculated $NO_3^-$ mg/l value from stage 1.

Loop for the range of hypochlorous in steps of 0.01 mg/l

Loop for the range of nitrate in steps of 0.1 mg/l

Loop for range 235 to 345 nm

Calculate the $NO_3^-$ absorbance value for each wavelength for intervals of 1 nm Calculate the HOCl absorbance value for each wavelength for intervals of 1 nm Sum the two.

Calculate the difference at each wavelength between the measured and the calculated absorbance.

Sum the square of the differences over the complete wavelength range.

If this is the smallest difference so far, store this number and the corresponding nitrate and hypochlorous value.

END

Figure 3:
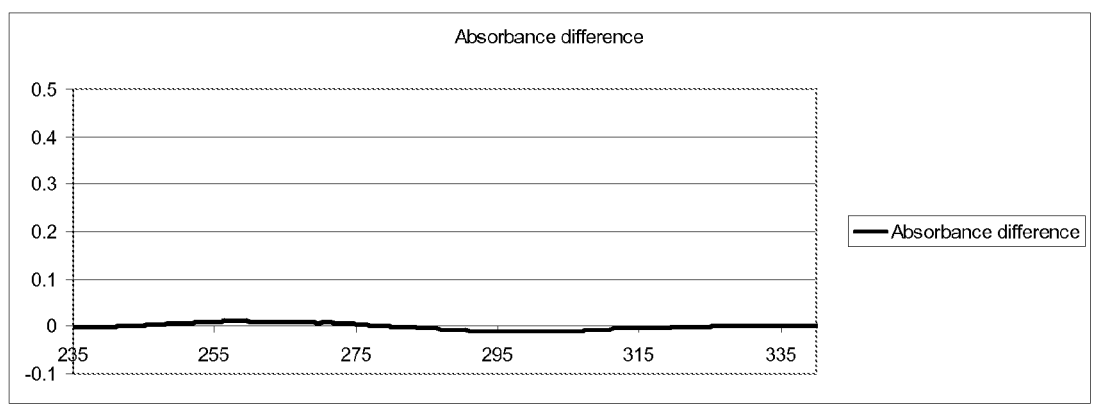
FIG. 3 shows a comparison of the concentrations of components in a known sample with those estimated by the method of the invention and FIG. 4 illustrates apparatus according to the invention.

FIG. 3 is a plot of the difference between an acquired UV spectrum for a sample of chlorine in water and a calculated spectrum (red) used according to the invention to estimate [HOCl], [OCl⁻] and [$NO_3^-$] in the sample.

The error associated with the method is barely discernible from this figure and table 2 indicates the errors in numerical form:

TABLE 2

|  | Calculated Values | Actual Values |
| --- | --- | --- |
| Nitrate mg/l | 30.0 | 30.0 |
| Hypochlorite mg/l | 0.15 | 0.15 |
| Hypochlorous mg/l | 0.97 | 0.95 |
| Free Chlorine mg/l | 1.13 | 1.10 |
| pH | 6.7 | 6.7 |

Figure 4:
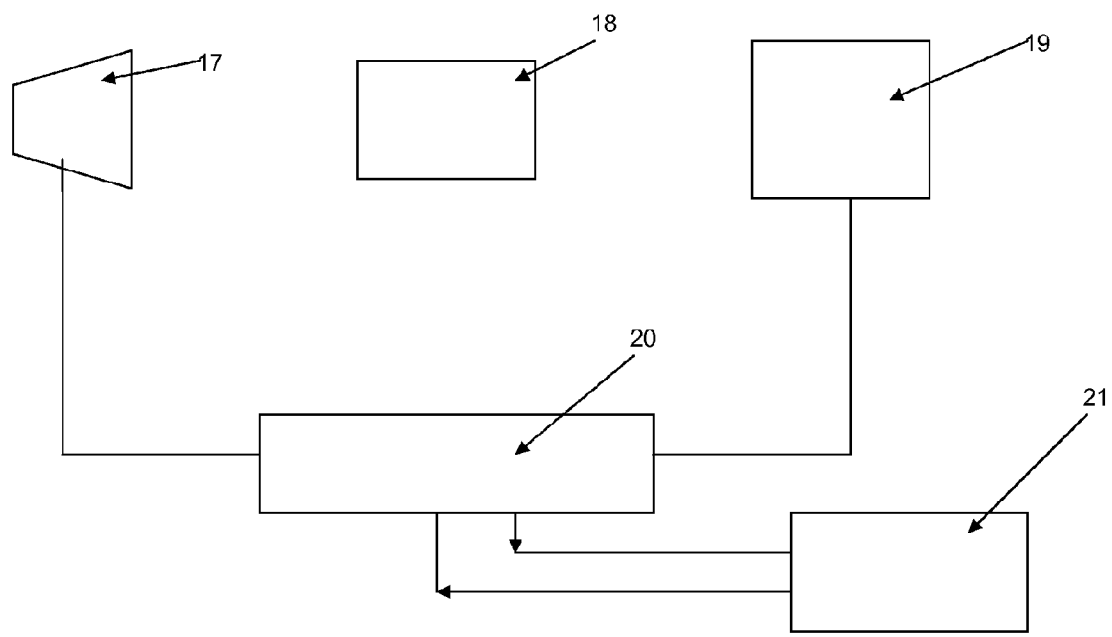

Referring to FIG. 4, a typical apparatus according to the invention includes a source 17 of radiation, a cell 18 for containing sample, arranged to be illuminated by the source 17 and suitable for allowing radiation to pass therethrough and a detector 19 arranged to detect radiation having passed through the cell and sample.

In a typical UV spectrometer, one might find a cell giving a path length of 10 mm but the present invention has been shown accurately to estimate component concentrations from spectra obtained using 20 cm, 50 cm and 100 cm. Alternatively, a spherical cell of the type known in the art, which provides an effective path length of many times its diameter, could be used.

Referring back to FIG. 4, the apparatus also includes a processor 20, able to control the radiation source 17 and the detector 19.

The apparatus also includes one or more machine readable data storage media 21 such as an optical or magnetic disc, which contains data representing a reference library of spectra for varying concentrations of the components of interest in the sample.

The storage media 21 also includes machine readable instructions for the processor to control the radiation source and detector during acquisition of a spectrum for the sample, and to perform the calculations comparisons and other steps which define the invention.

The processor 20 and storage medium 21 conveniently may be realised as part of a personal computer or other computing device, or they could be realised as an integral part of the equipment that is used in the field.

As an alternative to the configuration shown in FIG. 4, the apparatus may be realised as a separate spectrometer and computer, the latter receiving an acquired spectrum from the former and being able to perform the remaining steps of the invention.

The method of the invention has been illustrated with reference to nitrate ions, hypochlorite ions and hypochlorous acid but this should not be seen as limiting. In particular, the method of the invention is applicable to solutions containing ions giving rise to overlapping peaks in an absorption spectrum such as a UV or visible spectrum, including but not limited to peaks arising from:

Ozone (O3) based around a 254 nm absorption

Monochloramine (NH2Cl) based around a 243 nm absorption

Chlorine dioxide (ClO2) based around a 254 nm absorption

Potassium Permanganate based around a 520 nm absorption

Iodine (I2) based around absorption at 490 nm.

The invention claimed is:

1. A method of estimating the respective concentrations [X] and [Y] of at least two components, X and Y, in a solution, the method comprising:

acquiring absorption spectra for a plurality of solutions comprising variable concentrations of X and Y and thereby generating a library of reference data;

acquiring an absorption spectrum for the solution;

determining the wavelength, $\lambda_{max}$, at which maximum absorbance occurs within a first wavelength range of the absorbance spectrum for the solution; and comparing $\lambda_{max}$ with the reference data to derive first estimates of [X] and [Y].

2. The method of claim 1, further comprising:

defining first ranges of possible values for each of [X] and [Y], the ranges including the first estimates of [X] and [Y], respectively;

selecting a first set of pairs, each pair comprising a value from each of the first ranges;

for each pair, calculating a total theoretical absorbance at a plurality of wavelengths and extrapolating the theoretical absorbances so calculated, to produce a continuous theoretical absorption spectrum over a wavelength range substantially overlapping the range of the acquired spectrum of the solution;

comparing the continuous theoretical absorption spectra so obtained with the absorption spectrum of the solution; and selecting as second estimates of [X] and [Y], the members of the pair giving rise to the continuous theoretical absorption spectrum which most closely matches the absorption spectrum for the solution.

3. The method of claim 2, further comprising:

defining second ranges of possible values for each of [X] and [Y], the ranges including the second estimates of [X] and [Y], respectively;

selecting a second set of pairs, each pair comprising a value from each of the second ranges;

for each pair in the second set, calculating a total theoretical absorbance at a plurality of wavelengths and extrapolating the theoretical absorbances so calculated, to produce a continuous theoretical absorption spectrum over the wavelength range substantially overlapping the range of the acquired spectrum of the solution;

comparing the continuous theoretical absorption spectra so obtained with the absorption spectrum of the solution; and selecting as third estimates of [X] and [Y], the members of the pair giving rise to the continuous theoretical absorption spectrum which most closely matches the absorption spectrum for the solution.

4. The method of claim 2, further comprising:

calculating from the second estimate of [X], a theoretical absorbance due to X at a wavelength, $\lambda_2$, outside of the first wavelength range;

subtracting the theoretical absorbance so calculated from the absorbance at $\lambda_2$ indicated by the absorption spectrum for the solution, to yield an estimated absorption $A_Z$ at $\lambda_2$, attributable to a third component, Z, of the solution; and calculating from $A_Z$, a first estimate of [Z], the concentration of component Z in the solution.

5. The method of claim 4, further comprising:

defining a second range of possible values of [X], the second range including the second estimate of [X], and a first range of possible values of [Z], the first range including the first estimate of [Z];

selecting a second set of pairs, each pair comprising a value from the second range of possible values of [X] and a value from the first range of possible values of [Z];

for each pair in the second set, calculating a total theoretical absorbance at a plurality of wavelengths and extrapolating the theoretical absorbances so calculated, to produce a continuous theoretical absorption spectrum over the wavelength range substantially overlapping the range of the acquired spectrum of the solution;

comparing the continuous theoretical absorption spectra so obtained with the absorption spectrum of the solution and;

selecting as a third estimate of [X] and a second estimate of [Z], the members of the pair giving rise to the continuous theoretical absorption spectrum which most closely matches the absorption spectrum for the solution.

6. The method of claim 4, wherein the acquired absorption spectra are ultraviolet spectra.

7. The method of claim 6, where $X=NO_3^-$.

8. The method of claim 7, where $Y=OCl^-$.

9. The method of claim 8, where $Z=HOCl$.

10. The method of claim 4, wherein at least one of X, Y and Z is selected from:

ozone, monochloramine, chlorine dioxide, potassium permanganate and iodine.

11. An apparatus for estimating the respective concentrations [X] and [Y] of at least two components, X and Y, in a solution, the apparatus comprising:

a source of electromagnetic radiation of variable wavelength;

a cell suitable for retaining a sample of the solution and substantially transparent to the electromagnetic radiation;

a detector arranged to detect electromagnetic radiation radiated from the source and passing through the cell and sample;

a processor operable to vary the wavelength produced by the source of radiation and to store, in a computer readable data storage medium, data produced by the detector as the wavelength is varied, thereby generating an absorption spectrum for the solution;

wherein the computer readable data storage medium contains a library of reference data representing absorption spectra for a plurality of solutions comprising variable concentrations of X and Y; and wherein the processor is configured to determine the wavelength, $\lambda_{max}$, at which maximum absorbance occurs within a first wavelength range of the absorption spectrum for the solution and compare $\lambda_{max}$ with the library of reference data to derive first estimates of [X] and [Y].

12. The apparatus of claim 11, wherein the processor is further configured to:

define first ranges of possible values for each of [X] and [Y], the ranges including the first estimates of [X] and [Y], respectively;

select a first set of pairs, each pair comprising a value from each of the first ranges;

for each pair in the first set, calculate a total theoretical absorbance at a plurality of wavelengths and extrapolate the theoretical absorbances so calculated, to produce a continuous theoretical absorption spectrum over a wavelength range substantially overlapping the range of the acquired spectrum of the solution;

compare the continuous theoretical absorption spectra so obtained with the absorption spectrum of the solution; and select as second estimates of [X] and [Y], the members of the pair giving rise to the continuous theoretical absorption spectrum which most closely matches the absorption spectrum for the solution.

13. The apparatus of claim 12, wherein the processor is further configured to:

define second ranges of possible values for each of [X] and [Y], the ranges including the second estimates of [X] and [Y] respectively;

select a second set of pairs, each pair comprising a value from each of the second ranges;

for each pair in the second set, calculate a total theoretical absorbance at a plurality of wavelengths and extrapolate the theoretical absorbances so calculated, to produce a continuous theoretical absorption spectrum over the wavelength range substantially overlapping the range of the acquired spectrum of the solution;

compare the continuous theoretical absorption spectra so obtained with the absorption spectrum of the solution; and select as third estimates of [X] and [Y], the members of the pair giving rise to the continuous theoretical absorption spectrum which most closely matches the absorption spectrum for the solution.

14. The apparatus of claim 10, wherein the processor is further configured to:

calculate from the second estimate of [X] a theoretical absorbance due to X at a wavelength, $\lambda_2$, outside of the first wavelength range;

subtract the theoretical absorbance so calculated from the absorbance at $\lambda_2$ indicated by the absorption spectrum for the solution, to yield an estimated absorbance $A_Z$ at $\lambda_2$, attributable to a third component, Z, of the solution; and calculate from $A_z$, a first estimate of [Z], the concentration of component Z in the solution.

15. The apparatus of claim 14, further wherein the processor is further configured to:

define a second range of possible values of [X], the second range including the second estimate of [X], and a first range of possible values of [Z], the first range including the first estimate of [Z];

select a second set of pairs, each pair comprising a value from the second range of possible values of [X] and a value from the first range of possible values of [Z];

for each pair in the second set, calculate a total theoretical absorbance at a plurality of wavelengths and extrapolate the theoretical absorbances so calculated, to produce a continuous theoretical absorption spectrum over the wavelength range substantially overlapping the range of the acquired spectrum of the solution;

compare the continuous theoretical absorption spectra so obtained with the absorption spectrum of the solution; and select as a third estimate of [X] and a second estimate of [Z], the members of the pair giving rise to the continuous theoretical absorption spectrum which most closely matches the absorption spectrum for the solution.

16. The apparatus of claim 15, wherein the absorption spectra are ultraviolet.

17. The apparatus of claim 16, wherein the first range includes values between 250 nm and 330 nm.

18. The apparatus of claim 17, wherein the first range includes values between 290 nm and 320 nm.

19. The apparatus of claim 18, wherein $\lambda_2$ is between 235 nm and 245 nm.

20. The apparatus of claim 19, wherein the cell provides a path length for ultraviolet radiation of greater than 50 cm.

21. The apparatus of claim 19, wherein the cell provides a path length for ultraviolet radiation of greater than 100 cm.

* * * * *